United States Patent [19]

Cross et al.

[11] Patent Number: 4,868,024

[45] Date of Patent: Sep. 19, 1989

[54] MEDICO-SURGICAL AND SANITARY ARTICLES AND MATERIALS

[75] Inventors: David E. Cross, Rustington; John A. G. Gent, Liphook, both of England

[73] Assignee: Smiths Industries Public Limited Company, London, England

[21] Appl. No.: 82,607

[22] Filed: Aug. 7, 1987

[30] Foreign Application Priority Data

Aug. 28, 1986 [GB] United Kingdom ............... 8620778

[51] Int. Cl.$^4$ ............... B27N 5/02; B65D 30/08; A61F 5/44

[52] U.S. Cl. ............... 428/35.2; 428/35.4; 428/411.1; 428/515; 428/518; 428/522; 383/108; 383/109; 383/113; 604/332; 604/338

[58] Field of Search ............... 428/35, 411.1, 515, 428/520, 522, 518, 913, 35.2, 35.4; 383/105, 109, 113, 108; 604/332, 338, 368, 339, 333

[56] References Cited

U.S. PATENT DOCUMENTS

| | | | |
|---|---|---|---|
| 4,062,451 | 12/1977 | Gander | 428/286 |
| 4,186,233 | 1/1980 | Krajewski et al. | 428/213 |
| 4,190,562 | 2/1980 | Westerman | 523/111 |
| 4,242,408 | 12/1980 | Evani et al. | 428/290 |
| 4,469,728 | 9/1984 | Belz | 428/36 |
| 4,518,388 | 5/1984 | Jensen | 604/332 |
| 4,620,999 | 11/1986 | Holmes | 428/35 |

FOREIGN PATENT DOCUMENTS 1579919 11/1980 United Kingdom .
2083762 3/1982 United Kingdom .

Primary Examiner—Ellis P. Robinson
Assistant Examiner—Donald J. Loney
Attorney, Agent, or Firm—Pollock, Vande Sande and Priddy

[57] ABSTRACT

Sheet material for making a water closet disposable article, such as a bag for body waste products, is unaffected by contact with water of neutral pH, but is degraded on contact with an alkali added to the pan of the water closet. The material may have a central layer of polyvinyl alcohol, an inner layer made up of at least two coatings of a blend of polyvinylidene chloride acrylonitrile copolymer with carboxylated acrylic copolymer, and an outer layer of at least two coatings of carboxylated acrylic acid. A similar sheet can be used to back an absorbent layer of a sanitary article, such as a diaper. In use, an alkaline substance containing triethanolamine and a surfactant, such as sodium dioctyl sulphosuccinate, is added in liquid form to the water closet pan prior to dropping in the bag or other article, so as to raise the pH of the water to about 10.

14 Claims, 2 Drawing Sheets

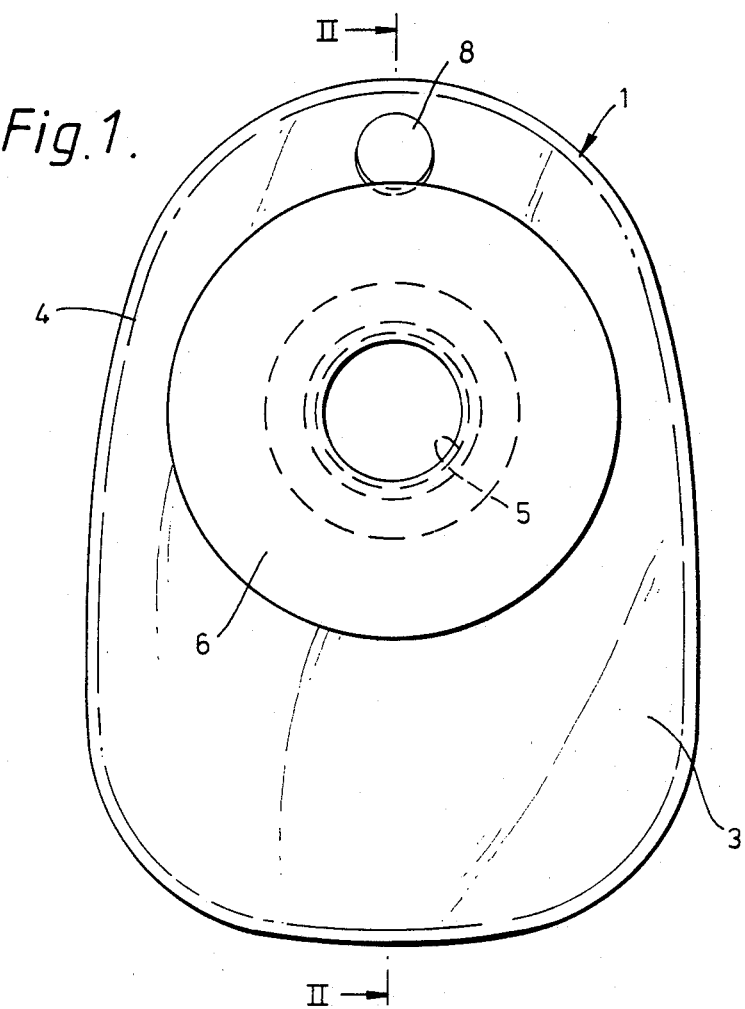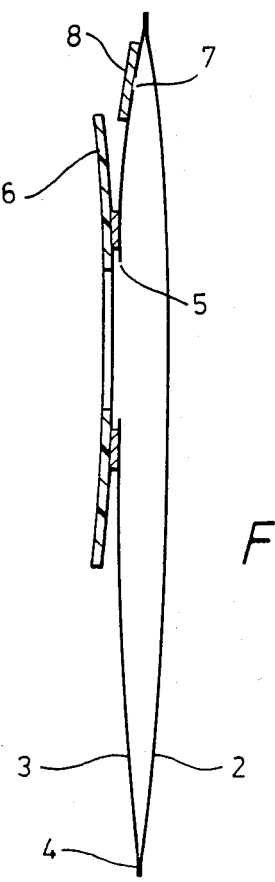

MEDICO-SURGICAL AND SANITARY ARTICLES AND MATERIALS

BACKGROUND OF THE INVENTION

This invention relates to medico-surgical and sanitary articles, and materials.

The invention is more particularly concerned with w.c. disposable articles, such as ostomy or urine incontinence bags, diapers, sanitary towels and so on and with materials from which they can be made which facilitate disposal of such articles.

Attempts have been made recently to develop ostomy and urine bags which can be disposed of by flushing in a water closet to avoid the need to make special disposal arrangements which can be inconvenient, embarrassing and unhygenic.

Disposable bags generally have an outer water soluble or dispersable layer and an inner water resistant layer. The outer layer provides mechanical support for the inner layer so that, when the bag is dropped into turbulent water in the pan of a water closet, the outer layer is quickly broken up. The inner layer prevents the contents of the bag attacking the outer layer in use but, once the outer layer is broken up on disposal, the inner layer does not have sufficient mechanical strength in itself to cause blockage on flushing the water closet. An example of such a bag is described in GB No. 2 83 762B.

Although such bags can be used satisfactorily, the fact that the outer layer is damaged by contact with water means that the user has to take special precautions to ensure the outside of the bag does not become wet. This can be especially inconvenient with bags which are worn long-term, for two or more days, such as is usually the case with ileostomy bags. The use of such a bag can make washing difficult.

An alternative form of bag is described in EP 0142950A which is made of 3-hydroxybutyrate film either in a laminate with a water soluble film as an outer layer, or entirely from 3-hydroxybutyrate. Such a material remains intact when in contact with water or body waste, but is broken up if the pH is raised to about 12. The bag described is disposed of by adding a base material to the contents of the bag so as to raise the pH of the contents to at least 12 so that it breaks up when agitated in a water closet pan. It will be appreciated that the laminated form of construction does not avoid the disadvantages referred to above of having to keep the outside of the bag dry. Where, however, the bag is made entirely of 3-hydroxybutyrate, this can be insensitive to external wetting. The method of disposal of such a bag, that is, by adding a base material to the contents of the bag, is not entirely satisfactory. Firstly, it can be distasteful to some users to have to open the bag in order to add the base chemical to it. Also, break up of the bag can be slow. This is because the bag will only be broken up where it is contacted by the alkali. If the bag is only partially full, as is usually the case, it follows that regions of the bag may remain untouched by the alkali. Furthermore, solid material such as faeces in the bag, will mask parts of the bag from attack by the alkali and thereby delay disposal. Also, if the contents of the bag are acid the strength of the alkali must be sufficient to counteract this which may require the use of a hazardly active alkali.

Similar problems are met with other articles, such as diapers. These preferably have an outer water-impermeable layer to reduce leakage, but this layer remains intact in a water closet, making disposal of such diapers more difficult.

BRIEF SUMMARY OF THE INVENTION

It is an object of the present invention, in its several aspects, to provide water closet disposable articles, materials from which these can be made, and methods of disposal of the articles which alleviate some at least of the above-mentioned disadvantages.

According to a first aspect of the present invention there is provided a water closet disposable bag for body waste products comprising a wall having a first layer that is inwardly presented to the contents of the bag, said first layer being resistant to the contents of the bag, and the second layer that is exposed on its outwardly presented surface, said second layer being substantially resistant to water at neutral pH, but being degraded on contact with alkali added to water in a water closet such as to render the first layer and the contents of the bag disposable in the water closet.

The wall preferably includes a third layer intermediate the first and second layers, the third layer being degraded on contact with water. The first and second layers may be coatings on opposite sides of the third layer. The third layer may contain cold water soluble polyvinyl alcohol. The first layer may be degraded on contact with alkali and may have insufficient inherent mechanical strength by itself to present any blockage to flushing of the water closet The said first layer may contain polvinylidene chloride acrylonitrile copolymer and carboxylated acrylic copolymer. The first and second layers may be of substantially the same composition. The second layer may contain carboxylated acrylic acid or polyvinylidene chloride and methyl acrylate. The first and second layer are preferably formed by at least two coatings on top of one another.

The bag may be a disposable ostomy bag including a water closet disposable flange by which the bag is secured to the patient.

According to a second aspect of the present invention there is provided sheet material for a water closet disposable bag, comprising a first layer exposed on one side of the sheet, the first layer being resistant to the bag contents, and a second layer exposed on the other side of the sheet, the second layer being substantially resistant to water at neutral pH, but being degraded by contact with an alkali added to water in the water closet.

The sheet material preferably includes a third layer intermediate the first and second layers, said third layer being degraded on contact with water. The said first and second layers may be coatings on opposite sides of the third layer. The third layer may contain cold water soluble polyvinyl alcohol. The first layer is preferably degraded on contact with alkali. The first layer may have insufficient inherent mechanical strength by itself to present any blockage to flushing of the water closet. The said first layer may contain polyvinylidene chloride acrylonitrile copolymer and carboxylated acrylic copolymer. The said first and second layers may be of substantially the same composition. The second layer may contain carboxylated acrylic acid or polyvinylidene chloride and methyl acrylate. The first and second layers are preferably formed by at least two coatings on top of another.

According to a third aspect of the present invention there is provided an article made from sheet material according to the above second aspect.

According to a fourth aspect of the present invention there is provided water closet disposable sheet material, comprising a central layer of a water degradable material, said central layer being faced on opposite sides with respective outer layers that are resistant to water at neutral pH, but that are degraded on contact with an alkali such that said sheet material can be disposed of in a water closet by adding an alkali to water in the water closet.

The said central layer may contain cold water soluble polyvinyl alcohol. At least one of the outer layers may contain carboxylated acrylic copolymer. The said outer layers may be coatings on the central layer and are preferably formed by at least two coatings on top of one another.

According to a fifth aspect of the present invention there is provided an article made from sheet material according to the above fourth aspect of the present invention.

According to a sixth aspect of the present invention there is provided an article of sanitary wear including a layer of absorbent material arranged to absorb body fluids and a sheet of material according to the above fourth aspect, extending over said layer of absorbent material on the side remote from the user such that said article can be disposed of in a water closet by adding an alkali to water in the w. c.

According to a seventh aspect of the present invention there is provided an article of sanitary wear including a layer of absorbent material arranged to absorb body fluids and a sheet of material extending over said layer of absorbent material on the side remote from the user, said sheet being resistant to said body fluids, but being degraded on contact with an alkali such that said article can be disposed of in a water closet by adding an alkali to water in the water closet.

According to an eighth aspect of the present invention there is provided a method of disposing of a water closet disposable article of the kind including a layer of material that is exposed or becomes exposed on the outer surface of the article, the layer being substantially resistant to water at neutral pH, but being degraded on contact with an alkali, including the steps of adding an alkaline substance to water in the w.c. pan so as to raise its pH, and placing the article in the water closet pan so that it is rendered disposable in the water closet by the action of the alkali in the water on the layer.

The pH of water in the water closet pan is preferably raised to about 10. The alkaline substance may be added to water in the water closet before placing the article in the pan. The alkaline substance may include triethanolamine and preferably includes a surfactant which may contain sodium dioctyl sulphosuccianate. The alkaline substance may be a liquid.

A water closet disposable ostomy bag, a article of sanitary wear, a material from which they are formed and a method of disposal of such a bag or article according to the present invention, will now be described, by way of example, with reference to the accompanying drawings.

BRIEF DESCRIPTION OF THE DRAWINGS

FIG. 1 is a plan view of the bag;

FIG. 2 is a sectional side elevation of the bag along the line II—II of FIG. 1

DESCRIPTION OF PREFERRED EMBODIMENTS

Figure 3:
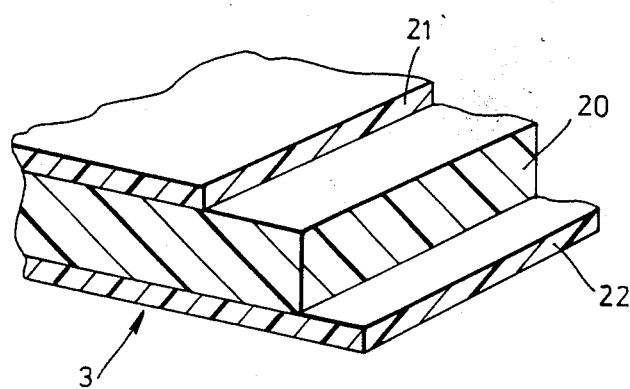
FIG. 3 is an enlarged perspective cut-away section through the wall of the bag.

With reference to FIGS. 1 and 2, the ostomy bag 1 is of conventional generally oblong shape and is formed from two walls 2 and 3 of the same flexible material that are joined together by welding around their edge 4 to form a sealed bag. An opening 5 is cut in one wall 3, towards its upper end, and an annular adhesive flange 6 has one face secured to the wall 3 around the opening 5, the other face of the flange being used to secure the bag to the patient's skin around the stoma. A vent 7 with a flatus filter 8 is provided above the opening 5 in the wall 3.

The construction of the material from which the bag 1 is made is novel and is shown if FIG. 3, although the thicknesses of the different layers are not shown to scale. The material of the walls 2 and 3 comprises three layers, that is, a central ply 20 with an inner coating 21 on one side, and an outer coating 22 on the opposite side. The inner coating 21 is exposed on its inner surface, that is, to the contents of the bag 1, while the outer coating 22 is exposed on the outer surface of the bag. The central ply 20 is of a cold water soluble polyvinyl alcohol of sufficient thickness to give the bag the desired degree of mechanical strength and impermeability to odor. The inner layer 21 is formed from a blend of polyvinylidene chloride acrylonitrile copolymer blended with 10-20% of a carboxylated acrylic copolymer which is coated on the inner surface of the central ply 20 to a thickness of about 5 gm$^{-2}$. It is preferable that the thickness of the layer 21 is built up by using at least two layers on top of one another so as to reduce the risk of pin hole apertures through the layer 21. The inner layer 21 formed in this way provides a flexible resistant barrier to the urine, faeces, or other body waste material in the bag 1, preventing it from dissolving the central ply 20. The material of the inner layer is, however, broken up on contact with an alkali. The inclusion of polyvinylidene chloride acrylonitrile copolymer in the layer 21 enables the inner layers of the two walls 2 and 3 to be welded to each other also gives layer 21 improved odor barrier properties. The inner layer 21 is preferably relatively thin so that it has little inherent mechanical strength, insufficient by itself to present any blockage to flushing of the water closet should this occur before the inner layer has been broken up.

The outer coating 22 is of a carboxylated acrylic acid such as sold by Allied Colloid (Ref. DP6-2651W) which is applied to the central ply 20 as a 50% solution in isopropanol. Alternatively, a blend of polyvinylidene chloride and methyl acrylate may be used. The outer coating 22 is built up to a thickness of 5 gm$^{-2}$ by two successive coatings of 2.5 gm$^{-2}$.

The outer coating 22 thus formed is resistant to water at neutral pH, but is quickly broken down by contact with an alkali. Other materials that are degraded on contact with an alkali could be used. By the term 'degraded' we include materials that are dissolved, dispersed or broken up.

The bag 1 formed from this material is thereby protected on its outer surface by the layer 22 which enables the bag to be worn by the user without risk of damage when it comes into contact with water. The user is thereby able to shower or swim without damage to the bag. This is of particular importance with bags which are worn for more than one day, such as used by ileostomy patients.

Figure 4:
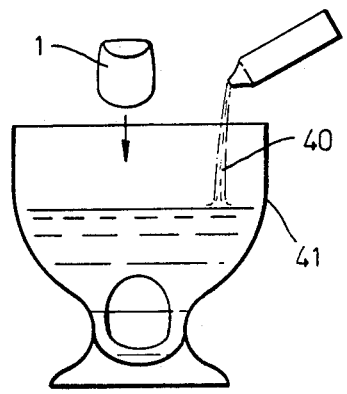
FIG. 4 illustrates the method of disposal of the bag.

The bag 1 is disposed of in a conventional water closet pan in the manner described below, with reference to FIG. 4.

The user first adds a quantity of a chemical 40 to the water in the water closet pan 41 which is sufficient to raise the pH of the water to about 10. The preferred chemical is a mixture of triethanolamine (a water soluble alkali) and a surfactant such as an ionic surfactant containing sodium dioctyl sulphosuccinate (e.g. Aerosol OT75—Aerosol is a Registered Trade Mark of Cyanamid) in the ratio 5:1 by weight-weight in water, it has a pH of 10 at 15 degrees Centigrade. The undiluted additive is therefore not too active to be dangerous to the user but needs only to be added in relatively small quantities to the water closet pan to be effective. The alkaline mixture is preferably in the form of a liquid which may be added to the water closet pan from a bottle, syringe, sachet or similar container. Alternatively, alkalis in the form of powders or tablets can be used which are dissolved on contact with water in the water closet pan.

The bag 1 is closed by folding the adhesive flange 6 in half about its diameter and excess air can be expelled by squeezing through the vent 7. The bag 1 is then dropped into the water closet pan 41 so that its outer surface is contacted by the alkali and water mixture. It will be appreciated that a large proportion of the bag surface quickly becomes wetted by the surfactant and alkali which starts to break up the outer layer 22. This allows the liquid in the water closet pan 41 to attack the central ply 20 through ruptures and dissolved apertures in the outer layer. After a few minutes in the pan 41 the outer layer 22 and central ply 20 are dissolved or dispersed allowing the inner layer to be broken up by the action of the alkali. Flushing of the water closet agitates the water in the pan 41 helping further to break up the inner layer 21 or force it into more intimate contact with the bag contents. Any residual gas in the bag 1 escapes through the filter 7 or through ruptures in the bag as the water closet is flushed, thereby allowing the contents of the bag and the remains of the bag itself to be flushed away without blockage.

The flange 6 is water closet disposable and, in this respect, may be of a material that becomes limp on contact with water and of a suitable size that is readily flushed away.

It will be appreciated that the alkali 40 may be added to the water closet pan 41 after, or at the same time as, adding the bag 1.

The three ply construction of the sheet material described above may be used for other water closet disposable articles such as bed pan liners.

Various alternative materials are possible. For example, the material of the inner layer need not be alkali degradable, but could be mechanically weak so that, when the central ply is broken up, the inner layer has insufficient mechanical strength by itself to impede disposal on flushing the water closet. In this respect, the inner layer might be ruptured by water pressure or collapse limply about the contents of the bag. In another alternative, the material could simply comprise a two ply construction, the outer ply being water insoluble, but alkali dispersable, and providing mechanical support for the inner layer which is of a different material and is water resistant.

The bag could have an outer cover of paper of other water permeable material, providing that the outer, alkali-degradable layer of the bag was still exposed to liquid in the water closet through the cover.

The method of disposing of a bag by adding an alkali to water in the water closet pan could be used with previous bags made from a single layer of an alkali disposable material. Adding the alkali to the water in the water closet pan ensures that the entire surface of the bag is rapidly contacted by the alkali, in contrast with previous disposal methods involving addition of an alkali to the bag contents.

Figure 5:
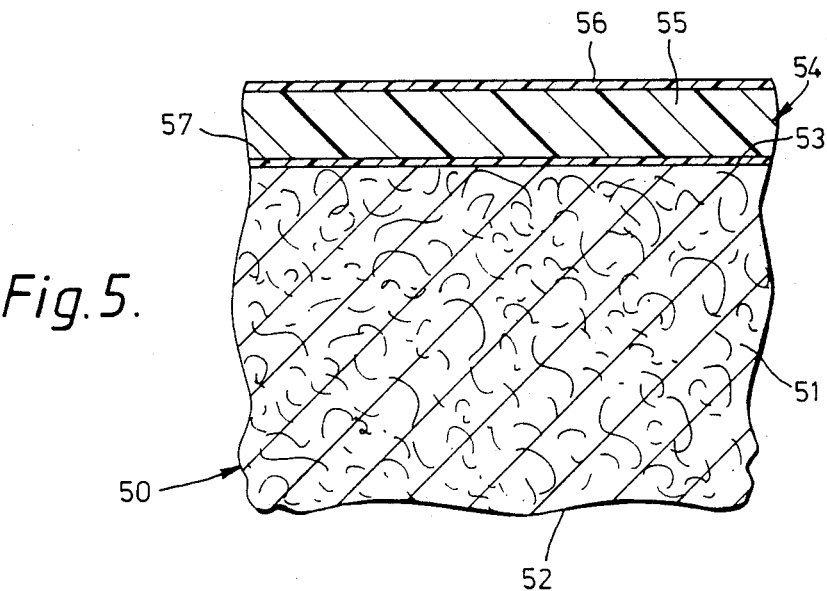
FIG. 5 is a sectional side elevation of an article of sanitary wear.

Similar methods could be used to dispose of other articles such as articles of sanitary wear of the kind shown in FIG. 5. This shows a baby's diaper 50 comprising a layer 51 of absorbent material, such a fabric, that is exposed on one side 51 to be in contact with the baby's skin. The layer 51 has a relatively low wet strength. The other side 53 is bonded to sheet 54 that is water 9 and urine) resistant so as to prevent leakage of urine from the diaper. The sheet 54 is, however, broken up by the action of an alkali added to a water closet pan. More particularly, the sheet 54 comprises a central ply 55 of a water soluble material (such as polyvinyl alcohol) that is coated on opposite sides with layers 56 and 57 of a material (such as carboxylated acrylic acid) that is water resistant, but that is dispersed or broken up by contact with an alkali. In use, the absorbent layer 51 absorbs urine while leakage is prevented by the sheet 54. The diaper 50 can be disposed of by placing in a water closet pan and adding an alkali. This produces a rapid break up of the sheet 54, in the manner described above which in turn allows the absorbent layer 51 to be broken up as it becomes saturated with water and loses strength.. It will be appreciated that a similar construction could be used with other articles of sanitary wear such as absorbent pads and feminine sanitary towels.

What we claim is:

1. A water closet disposable bag for body waste products having a water closet disposable wall, said wall having a central layer of a cold-water soluble polymeric material, a continuous inner layer which is presented inwardly to the contents of the bag and which is resistant to the contents of the bag, and a continuous outer layer, said outer layer being provided over the entire outer surface of said central layer and being fabricated of a material including a carboxylated acrylic polymer such that said outer layer is substantially resistant to water at neutral pH but is degradable on contact with an alkali added to water in a water closet thereby to render the bag and any contents disposable in the water closet.

2. A water closet disposable bag according to claim 1, wherein said outer layer is provided by a coating on the outer surface of said central layer.

3. A water closet disposable bag according to claim 1, wherein the central layer is of polyvinyl alcohol.

4. A water closet disposable bag according to claim 1, wherein said inner layer is of a material including a carboxylated acrylic polymer.

5. A water closet disposable bag according to claim 4 wherein said inner layer is a blend of a carboxylated acrylic polymer and a polyvinylidene chloride copolymer.

6. A water closet disposable ostomy bag having a water closet disposable wall, said wall having a central layer of a cold-water soluble polymeric material, a continuous inner layer which is presented inwardly to the contents of the bag an which is resistant to the contents of the bag, and a continuous outer layer that defines the outwardly presented surface of said wall, said outer layer being substantially resistant to water at neutral pH but being degradable on contact with an alkali added to water in a water closet such as to render the bag and any contents disposable in a water closet, at least one of said continuous inner and outer layers being a blend of a first and second substance, said first substance being degradable on contact with an alkali and said second substance being a polyvinylidene chloride copolymer.

7. A water closet disposable ostomy bag according to claim 6 wherein said central layer is of polyvinyl alcohol.

8. A water closet disposable ostomy bag according to claim 6 wherein said inner layer is a blend of said first substance and a polyvinylidene copolymer.

9. A water closet disposable ostomy bag according to claim 8 wherein said outer layer includes a carboxylated acrylic polymer.

10. Water closet disposable sheet material comprising a central layer of a cold-water soluble polymeric material and two continuous outer layers on opposite sides respectively of said central layer, said two outer layers both being provided by coatings that completely cover said central layer, said coatings being of a material including a carboxylated acrylic polymer such that said outer layers are resistant to water at neutral pH but are degraded when contacted by an alkali whereby the sheet material can be disposed of in a water closet by adding an alkali to water in the water closet.

11. Water closet disposable sheet material according to claim 16 wherein said central layer is of polyvinyl alcohol.

12. Water closet disposable sheet material according to claim 10 wherein at least one of said outer layers is a blend of carboxylated acrylic polymer and a substance that is substantially impermeable to odor during use.

13. Water closet disposable sheet material according to claim 10 wherein at least one of said outer layers is a blend of carboxylated acrylic polymer and a polyvinylidene chloride copolymer.

14. A water closet disposable article including water closet disposable sheet material according to claim 10.

* * * * *